United States Patent
Ojio et al.

[11] Patent Number: 6,140,438
[45] Date of Patent: *Oct. 31, 2000

[54] SOFT INTRAOCULAR LENS MATERIAL

[75] Inventors: Tatsuya Ojio; Kazuharu Niwa; Tohru Kawaguchi, all of Kasugai, Japan

[73] Assignee: Menicon Co., Ltd., Nagoya, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/132,055

[22] Filed: Aug. 11, 1998

[30] Foreign Application Priority Data

Aug. 20, 1997 [JP] Japan .................................. 9-224049

[51] Int. Cl.⁷ .................................................. C08F 226/10

[52] U.S. Cl. .................... 526/264; 526/307.5; 526/307.7; 526/320

[58] Field of Search .............................. 526/320, 318.42, 526/264, 303.1, 328.5, 307.5, 307.7; 623/6

[56] References Cited

U.S. PATENT DOCUMENTS

| | | |
|---|---|---|
| 4,036,814 | 7/1977 | Howes et al. . |
| 4,216,303 | 8/1980 | Novicky . |
| 4,365,074 | 12/1982 | Novicky . |
| 4,620,954 | 11/1986 | Singer et al. . |
| 4,749,761 | 6/1988 | Howes . |
| 4,889,664 | 12/1989 | Kindt-Larsen et al. . |
| 5,026,807 | 6/1991 | Ohira et al. ............................. 526/320 |
| 5,039,459 | 8/1991 | Kindt-Larsen et al. . |
| 5,216,101 | 6/1993 | Kawanaka et al. ...................... 526/320 |
| 5,331,073 | 7/1994 | Weinschenk, III et al. . |
| 5,543,463 | 8/1996 | Kitaike et al. ........................... 526/320 |
| 5,563,227 | 10/1996 | Kitaike et al. ........................... 526/320 |
| 5,693,095 | 12/1997 | Freeman et al. . |
| 5,712,356 | 1/1998 | Bothe et al. ............................. 526/320 |
| 5,824,719 | 10/1998 | Kumzler et al. ........................ 526/320 |

Primary Examiner—Bernard Lipman
Attorney, Agent, or Firm—Oblon, Spivak, McClelland, Maier & Neustadt, P.C.

[57] ABSTRACT

A soft intraocular lens material which consists essentially of a polymer obtained by polymerizing polymerizable components containing a hydrophilic monomer, and which has a water absorptivity of from 1.5 to 4.5 wt %.

20 Claims, No Drawings

SOFT INTRAOCULAR LENS MATERIAL

The present invention relates to a soft intraocular lens material. More specifically, it relates to a soft intraocular lens material which is excellent in flexibility and has a high refractive index, whereby the lens can be made thin and can be folded so that it can be inserted through a small incision, and which is yet excellent in transparency and free from so-called glistenings i.e. a phenomenon whereby such transparency is lost.

In order to minimize the injury to the eye by cataract operation using an intraocular lens, it is usually advisable to minimize the incision for the surgical operation. As phacoemulsification has progressed wherein a crystalline lens is fractured by ultrasonic vibration, and its fragments are suctioned by means of a small cannula, it has been made possible to remove a crystalline lens through an incision not larger than 2 or 3 mm.

However, an intraocular lens usually has a diameter of about 6 mm, and to insert such an intraocular lens as it is, it is necessary to incise the portion for insertion to a large extent. Accordingly, in recent years, various intraocular lenses of soft type which are soft, flexible and swellable, have been invented, whereby insertion through a small incision has been made possible.

As such intraocular lenses, there have been proposed, for example, an intraocular lens obtained by copolymerizing a monomer mixture comprising at least two types of (meth) acrylate monomers having aromatic rings, and a crosslinkable monomer (JP-A-4-292609), a soft intraocular lens obtained by using components comprising a perfluorooctyl-ethyloxypropylene (meth)acrylate monomer, a 2-phenylethyl (meth)acrylate monomer, an alkyl (meth) acrylate and a crosslinkable monomer (JP-A-8-224295), and an intraocular lens obtained by using a monomer, of which the refractive index of the homopolymer is at least 1.5, a monomer, of which the glass transition temperature of the homopolymer is lower than 30° C., and a crosslinkable monomer (JP-A-8-503506).

Each of these intraocular lenses has transparency and flexibility and is deformable, and each of them can accordingly be inserted through a relatively small incision. However, they have a drawback that when they are implanted in the eyes, white dots appear in the lenses by hydration, whereby so-called glistenings take place i.e. a phenomenon whereby the transparency is substantially lowered or lost.

In addition to those mentioned above, for example, an intraocular lens material employing a hydroxyalkyl (meth) acrylate and a ring structure- or halogen atom-containing (meth)acrylate and/or (meth)acrylamide derivative as the main components (JP-A-6-22565), an ocular lens material for e.g. an intraocular lens, obtained by using a composition comprising a (meth)acrylate having a hydroxyl group and a phenoxy group which may be substituted, and a crosslinking agent (JP-A-8-173522), and a soft intraocular lens material employing an aromatic ring-containing acrylate and a fluorine atom-containing alkyl acrylate as the main components (JP-A-9-73052), have been proposed.

Each of these materials is excellent in flexibility and has a large shape-regaining force and thus can be inserted through a small incision. However, when they are implanted in the eyes, their transparency likewise tends to decrease by a temperature change. Therefore, it has been desired to develop an intraocular lens which is free from such a decrease in the transparency (glistenings).

The present invention has been made in view of the above-mentioned prior art, and it is an object of the present invention to provide a soft intraocular lens material which is excellent in flexibility and has a high refractive index, whereby the lens can be made thin and can be folded and inserted through a small incision, and which is capable of presenting a soft intraocular lens which is excellent in transparency and free from glistenings.

The present invention provides a soft intraocular lens material which consists essentially of a polymer obtained by polymerizing polymerizable components containing a hydrophilic monomer, and which has a water absorptivity of from 1.5 to 4.5 wt %.

Now, the present invention will be described in detail with reference to the preferred embodiments.

As mentioned above, the soft intraocular lens material of the present invention consists essentially of a polymer obtained by polymerizing polymerizable components containing a hydrophilic monomer, and has a water absorptivity of from 1.5 to 4.5 wt %.

The most important object of the present invention is to provide a material which is capable of providing a soft intraocular lens having excellent properties such that it shows excellent transparency and is free from glistenings. Heretofore, various researches relating to maintenance of excellent transparency have been made, since the transparency of e.g. an acrylic soft intraocular lens tends to gradually decrease and in some cases, be lost to such an extent as to cause a problem in the viewing function, when such an intraocular lens is implanted in the eye. Here, the present inventors have conducted an extensive study by paying a particular attention to the temperature change before and after the implantation of the intraocular lens, the relation between the water content in the material of the intraocular lens and the glistenings, and the relation between agglomeration of water in the material due to the temperature change and the glistenings. As a result, it has been found possible to obtain a material whereby excellent transparency can be maintained without glistenings in spite of a temperature change, on the basis of a concept such that by incorporating or uniformly dispersing units based on a hydrophilic monomer, as constituting units in a material having a low water absorptivity which is usually susceptible to glistenings, the contained water is also dispersed, and agglomeration of water (glistenings) will not take place.

The polymer to be used in the present invention is one obtained by polymerizing polymerizable components containing a hydrophilic monomer (hereinafter referred to as the hydrophilic monomer (B)).

The hydrophilic monomer (B) becomes essential constituting units in the resulting soft intraocular lens material, as mentioned above, and is a component having a function to promote the lowering of glistenings in the soft intraocular lens material.

Typical examples of the hydrophilic monomer (B) include a hydroxyl group-containing alkyl (meth)acrylate wherein the alkyl group has from 1 to 20 carbon atoms (hereinafter referred to as a monomer (B-1), a (meth) acrylamide monomer (hereinafter referred to as a monomer (B-2)), an N-vinyl lactam (hereinafter referred to as a monomer (B-3)), and a hydrophilic monomer (hereinafter referred to as a monomer (B-4)) other than such monomers (B-1), (B-2) and (B-3). At least one member selected from these monomers can be suitably used.

The monomer (B-1) may, for example, be a hydroxyalkyl (meth)acrylate such as hydroxyethyl (meth)acrylate, hydroxypropyl (meth)acrylate, hydroxybutyl (meth)acrylate or hydroxypentyl (meth)acrylate; or a dihydroxyalkyl (meth)acrylate such as dihydroxypropyl (meth)acrylate, dihydroxybutyl (meth)acrylate or dihydroxypentyl (meth)acrylate. These monomers can be used alone or in combination as a mixture of two or more of them.

The monomer (B-2) may, for example, be an N,N-dialkyl (meth)acrylamide such as N,N-dimethyl (meth)acrylamide, N,N-diethyl (meth)acrylamide or N,N-dipropyl (meth)acrylamide; or an N,N-dialkylaminoalkyl (meth)acrylamide such as N,N-dimethylaminopropyl (meth)acrylamide or N,N-diethylaminopropyl (meth)acrylamide. These monomers may be used alone or in combination as a mixture of two or more of them.

The monomer (B-3) may, for example, be N-vinylpyrrolidone, N-vinylpiperidone or N-vinylcaprolactam. These monomers may be used alone or in combination as a mixture of two or more of them.

The monomer (B-4) may, for example, be diethylene glycol mono(meth)acrylate, triethylene glycol mono (meth)acrylate, propylene glycol mono (meth)acrylate, (meth)acrylic acid, methoxyethyl (meth)acrylate, ethoxyethyl (meth)acrylate, maleic anhydride, maleic acid, a maleic acid derivative, fumaric acid, a fumaric acid derivative, an aminostyrene or a hydroxystyrene. These monomers may be used alone or in combination as a mixture of two or more of them.

Among the above hydrophilic monomers (B), the above monomers (B-1) and (B-2) are preferred, and 2-hydroxyethyl methacrylate is particularly preferred, since the function to promote the lowering of glistening is large.

In order to sufficiently obtain the effect to promote the lowering of glistenings, the content of the hydrophilic monomer (B) in the polymerizable components, is usually at least 7 wt %, preferably at least 10 wt %. Further, in order to eliminate the possibility of a decrease in the flexibility or a decrease in the refractive index or the shape-restoration property of the soft intraocular lens material, it is usually at most 45 wt %, preferably at most 42 wt %.

The polymerizable components to obtain the polymer to be used in the present invention, may contain, in addition to the above hydrophilic monomer (B) other polymerizable monomers copolymerizable with such a hydrophilic monomer (B), as the case requires.

Typical examples of such other polymerizable monomers include an aromatic ring-containing (meth)acrylate (hereinafter referred to as a (meth)acrylate (A)) of the formula (I):

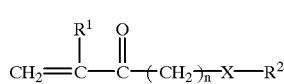

(I)

wherein $R^1$ is a hydrogen atom or a methyl group, $R^2$ is an aromatic ring which may be substituted by at least one substituent, such as a $C_{1-10}$ alkyl group or a halogen atom such as a fluorine atom, a chlorine atom or a bromine atom, X is an oxygen atom or a direct bond, and n is an integer of from 0 to 5, an alkyl (meth)acrylate wherein the alkyl group has from 1 to 20 carbon atoms (hereinafter referred to as an alkyl (meth)acrylate (C)) other than the above-mentioned monomer (B-1), and a crosslinkable monomer (hereinafter referred to as a crosslinkable monomer (D)).

The above (meth)acrylate (A) is a component having a function to improve the refractive index of the resulting soft intraocular lens material.

Specific examples of the (meth)acrylate (A) include phenoxyethyl (meth)acrylate, phenylethyl (meth)acrylate, benzyl (meth)acrylate, phenyl (meth)acrylate and pentabromophenyl (meth)acrylate. These acrylates may be used alone or in combination as a mixture of two or more of them. Among them, it is preferred to use at least one member selected from phenoxyethyl acrylate, phenylethyl acrylate and benzyl acrylate, as the effect to improve the refractive index of the resulting soft intraocular lens material is large. Particularly preferred is phenoxyethyl acrylate, since in addition to the above refractive index, the flexibility can also be improved.

The above alkyl (meth)acrylate (C) is a component having a function to improve the flexibility and the shape restoration property of the soft intraocular lens material.

Specific examples of the alkyl (meth)acrylate (C) include a linear, branched or cyclic alkyl (meth)acrylate such as methyl acrylate, ethyl acrylate, propyl acrylate, butyl acrylate, pentyl acrylate, hexyl acrylate, heptyl acrylate, nonyl acrylate, stearyl (meth)acrylate, octyl (meth)acrylate, decyl (meth)acrylate, lauryl (meth)acrylate, pentadecyl (meth)acrylate, 2-ethylhexyl (meth)acrylate, cyclopentyl acrylate or cyclohexyl acrylate; and a fluorine-containing alkyl (meth)acrylate such as 2,2,2-trifluoroethyl (meth)acrylate, 2,2,3,3-tetrafluoropropyl (meth)acrylate, 2,2,3,3-tetrafluoro-t-pentyl (meth)acrylate, 2,2,3,4,4,4-hexafluorobutyl (meth)acrylate, 2,2,3,4,4,4-hexafluoro-t-hexyl (meth)acrylate, 2,3,4,5,5,5-hexafluoro-2,4-bis(trifluoromethyl)pentyl (meth)acrylate, 2,2,3,3,4,4-hexafluorobutyl(meth)acrylate, 2,2,2,2', 2', 2'-hexafluoroisopropyl (meth)acrylate, 2,2,3,3,4,4,4-heptafluorobutyl (meth)acrylate or 2,2,3,3,4,4,5,5-octafluoropentyl (meth)acrylate. These compounds may be used alone or in combination as a mixture of two or more of them. Among these compounds, preferred is an alkyl acrylate wherein the alkyl group has from 1 to 5 carbon atoms, and particularly preferred is ethyl acrylate and/or butyl acrylate, since the effect to improve the flexibility and the shape restoration property of the resulting soft intraocular lens material is large.

The above crosslinkable monomer (D) is a component having a function to impart good mechanical strength, to further improve the shape restoration property or to improve the copolymerizability of the hydrophilic monomer (B) or the polymerizable components such as other polymerizable monomers to one another.

Specific examples of the crosslinkable monomer (D) include butanediol di(meth)acrylate, ethylene glycol di(meth)acrylate, diethylene glycol di(meth)acrylate, triethylene glycol di(meth)acrylate, propylene glycol di(meth)acrylate, dipropylene glycol di(meth)acrylate, diallyl fumarate, allyl (meth)acrylate, vinyl (meth)acrylate, trimethylolpropane tri(meth)acrylate, methacryloyloxyethyl (meth)acrylate, divinylbenzene, diallylphthalate, diallyl adipate, triallyl diisocyanate, α-methylene-N-vinylpyrrolidone, 4-vinylbenzyl (meth)acrylate, 3-vinylbenzyl (meth)acrylate, 2,2-bis((meth)acryloyloxyphenyl)hexafluoropropane, 2,2-bis((meth)acryloyloxyphenyl)propane, 1,4-bis(2-(meth)acryloyloxyhexafluoroisopropyl)benzene, 1,3-bis(2-(meth)acryloyloxyhexafluoroisopropyl)benzene, 1,2-bis(2-(meth)acryloyloxyhexafluoroisopropyl)benzene, 1,4-bis(2-(meth)acryloyloxy isopropyl)benzene, 1,3-bis(2-(meth)acryloyloxyisopropyl)benzene and 1,2-bis(2-(meth)acryloyloxyisopropyl)benzene. These monomers may be used alone or in combination as a mixture of two or more of them. Among them, butanediol di(meth)acrylate and ethylene glycol di(meth)acrylate are particularly preferred from the viewpoint such that the effect to impart good mechanical strength and to improve the copolymerizability and the shape restoration property, is large.

It is preferred to suitably adjust the content of such other polymerizable monomers in the polymerizable components, so that the effect by the above hydrophilic monomer (B) is sufficiently obtained, so that the effects of the respective polymerizable monomers can adequately be obtained and so that the copolymerizability of the polymerizable components to one another is maintained, and it is adjusted so that the total amount of the polymerizable components inclusive of the hydrophilic monomer (B), will be 100 wt %. Namely, the content of other polymerizable monomers in the polymerizable components is usually at least 55 wt %, preferably at least 58 wt %, and usually at most 93 wt %, preferably at most 90 wt %.

In the present invention, it is particularly preferred to employ a polymer obtained by polymerizing polymerizable components comprising the above (meth)acrylate (A)), at least one hydrophilic monomer (B) selected from the monomers (B-1), (B-2) and (B-3), the alkyl (meth)acrylate (C) and the crosslinkable monomer (D), since the effects to improve the flexibility of the resulting soft intraocular lens material, to impart a high refractive index and to maintain the excellent transparency irrespective of the temperature change, without glistenings, can be obtained more remarkably.

When the (meth)acrylate (A), the hydrophilic monomer (B), the alkyl (meth)acrylate (C) and the crosslinkable monomer (D) are used in combination as mentioned above, the amounts of the respective components are preferably adjusted as follows.

In order to adequately increase the refractive index of the resulting soft intraocular lens material, the weight ratio of the (meth)acrylate (A) to the alkyl (meth)acrylate (C) (i.e. the (meth)acrylate (A)/the alkyl (meth)acrylate (C)), is preferably adjusted to be at least 10/90, preferably at least 15/85. Further, in order to adequately obtain the effect to improve the shape restoration property of the soft intraocular lens material and the effect to control the flexibility, the weight ratio is preferably adjusted to be at most 95/5, preferably at most 80/20.

Further, the amount of the above hydrophilic monomer (B) is preferably adjusted to be at least 10 parts by weight, preferably at least 13 parts by weight, per 100 parts by weight of the total amount of the (meth)acrylate (A) and the alkyl (meth)acrylate (C), in order to adequately obtain the effect to promote the lowering of glistenings, and it is preferably adjusted to be at most 45 parts by weight, preferably at most 42 parts by weight, per 100 parts by weight of the above total amount, in order to eliminate the possibility of a decrease in the refractive index and the shape restoration property of the soft intraocular lens material or a decrease in the flexibility.

Further, the amount of the above crosslinkable monomer (D) is preferably adjusted to be at least 0.1 part by weight, preferably at least 0.5 part by weight, per 100 parts by weight of the total amount of the (meth)acrylate (A) and the alkyl (meth)acrylate (C) in order to control the flexibility of the resulting soft intraocular lens material and to adequately obtain the effect to improve the copolymerizability and the shape restoration property. Further, it is preferably adjusted to be at most 10 parts by weight, preferably at most 5 parts by weight, per 100 parts by weight of the above total amount, in order to eliminate the possibility of a decrease in the flexibility of the soft intraocular lens material or a decrease in the shape restoration property.

Further, in the present invention, from the viewpoint of safety, an ultraviolet absorber or a dyestuff which scarcely elutes from the soft intraocular lens material, may be added to the polymerizable components, as the case requires.

Typical examples of the ultraviolet absorber include benzophenones such as 2-hydroxy-4-methoxybenzophenone and 2-hydroxy-4-octoxybenzophenone, benzotriazoles such as 2-(2'-hydroxy-5'-methacryloxyethyleneoxy-t-butylphenyl)-5-methyl-benzotriazole, 2-(2'-hydroxy-5'-methylphenyl)benzotriazole and 5-chloro-2(3'-t-butyl-2'-hydroxy-5"-methylphenyl)benzotriazole, salicylic acid derivatives, and hydroxyacetophenone derivatives. Further, a reactive ultraviolet absorber may also be employed which has the same chemical structure portion as the above-mentioned ultraviolet absorbers and which as a portion polymerizable with the polymerizable components in the present invention. These ultraviolet absorbers may be used alone or in combination as a mixture of two or more of them.

The amount of the ultraviolet absorber is preferably adjusted to be at least 0.01 part by weight, preferably at least 0.05 part by weight, per 100 parts by weight of the total amount of the polymerizable components, and it is preferably adjusted to be at most 5 parts by weight, preferably at most 3 parts by weight, per 100 parts by weight of the total amount of the polymerizable components.

The above dyestuff is preferably a yellow or orange dyestuff, in order to correct, by the soft intraocular lens, blue vision of a patient having no crystalline lens after the cataract operation. Typical examples of such a dyestuff include an oil-soluble dyestuff such as CI Solvent Yellow or CI Solvent Orange as disclosed in Color Index (CI), a disperse dye such as CI Disperse Yellow or CI Disperse Orange, and a bat dye. Further, it is also possible to use a reactive dye which has same chemical structural portion as these dyes and which has a portion polymerizable with the polymerizable components of the present invention. These dyestuffs may be used alone on in combination as a mixture of two or more of them.

The amount of the above dyestuff is preferably adjusted to be at least 0.001 part by weight, preferably at least 0.01 part by weight, per 100 parts by weight of the total amount of the polymerizable components, so that the resulting soft intraocular lens material is sufficiently colored. Further, it is preferably adjusted to be at most 5 parts by weight, preferably at most 3 parts by weight, per 100 parts by weight of the total amount of the polymerizable components, so that the material will not be excessively deeply colored.

The soft intraocular lens material of the present invention can be obtained by blending, if necessary, a ultraviolet absorber or a dyestuff to the polymerizable components comprising the hydrophilic monomer (B) and, if necessary, other polymerizable monomers, and then adding e.g. a radical polymerization initiator thereto, followed by polymerization by a usual method.

The usual method may, for example, be a method which comprises incorporating a radical polymerization initiator which is commonly used for polymerization, to the polymerizable components and then gradually heating the mixture within a temperature range of from room temperature to about 130° C., or a method which comprises irradiating electromagnetic waves such as microwaves, ultraviolet rays or radiation rays (γ-rays) to carry out the polymerization. In the case of the heat polymerization, the temperature may stepwisely be raised. Further, the polymerization may be conducted by a bulk polymerization method or a solvent polymerization method by means of a solvent, or it may be conducted by any other methods.

Typical examples of the above radical polymerization initiator include azobisisobutyronitrile, azobisdimethylvaleronitrile, benzoyl peroxide, t-butyl hydroperoxide, and cumene hydroperoxide. These initiators may be used alone or in combination as a mixture of two or more of them.

In a case where polymerization is carried out by means of light rays, a photopolymerization initiator or a sensitizer may preferably be incorporated.

Typical examples of the above photopolymerization initiator include benzoin type photopolymerization initiators such as methylorthobenzoyl benzoate, methylbenzoyl formate, benzoin methyl ether, benzoin ethyl ether, benzoin isopropyl ether, benzoin isobutyl ether and benzoin n-butyl ether; phenone type photopolymerization initiators such as 2-hydroxy-2-methyl-1-phenylpropan-1-one, p-isopropyl-α-hydroxyisobutylphenone, p-t-butyltrichloroacetophenone, 2,2-dimethoxy-2-phenylacetophenone, α, α-dichoro-4-phenoxyacetophenone and N,N-tetraethyl-4,4-diaminobenzophenone; 1-hydroxycyclohexylphenylketone; 1-phenyl-1,2-propanedione-2-(o-ethoxycarbonyl)oxime; thioxanthone type photopolymerization initiators such as 2-chlorothioxanthone and 2-methylthioxanthone; dibenzosuberone; 2-ethylanthraquinone; benzophenone acrylate; benzophenone; and benzyl.

The amount of the above polymerization initiator or the sensitizer is preferably adjusted to be at least 0.002 part by weight, preferably at least 0.01 part by weight, per 100 parts by weight of the total amount of the polymerizable components to let the polymerization reaction proceed at an adequate rate. Further, it is preferably adjusted to be at most 10 parts by weight, preferably at most 2 parts by weight, per 100 parts by weight of the polymerizable components to prevent formation of bubbles in the resulting soft intraocular lens material.

When the soft intraocular lens material of the present invention is shaped into soft intraocular lenses, shaping methods which are commonly employed by those skilled in the art, may be employed. As such shaping methods, a cutting and grinding method and a molding method may, for example, be mentioned. The cutting and grinding method is a method in which polymerization of the polymerizable components is carried out in a suitable mold or vessel designed to facilitate shaping of an intraocular lens, to obtain a rod-, block- or plate-shaped base material (polymer), and then the base material is processed into a desired shape by mechanical processing such as cutting, grinding and polishing. The molding method is a method wherein a mold corresponding to the shape of a desired intraocular lens is prepared, and the polymerization of the above polymerizable components is carried out in this mold to obtain a polymer (a molded product), which may further be subjected to mechanical finishing treatment, if necessary. The above-mentioned mold or vessel wherein polymerization of the polymerizable components is carried out, may be one made of glass or a plastic such as polyethylene or polypropylene.

Apart from these methods, in the present invention, it is also possible to employ a method wherein a monomer capable of imparting a hard nature is impregnated to a soft intraocular lens material, then the monomer is polymerized to harden the entire material, which is then subjected to cutting and grinding to obtain a shaped product processed to have a desired shape, whereupon the hard polymer is removed from the shaped product to obtain a shaped product (a soft intraocular lens) made of a soft intraocular lens material (JP-A-62-278041, JP-A-1-11854).

When a soft intraocular lens is prepared from the soft intraocular lens material of the present invention, a supporting portion of the lens may be prepared separately from the lens, and a hole may be formed in the lens so that the supporting portion may be attached to the lens by inserting it into the hole, or it may be molded simultaneously (integrally) with the lens.

The soft intraocular lens material of the present invention thus obtainable, has a water absorptivity of from 1.5 to 4.5 wt %. As mentioned above, it is a non-water absorptive material having such a specific water absorptivity and containing units based on a hydrophilic monomer (B) as constituting units, whereby the excellent transparency can be maintained without glistenings, which are likely to take place with conventional materials. If the water absorptivity of such a soft intraocular lens material is less than 1.5 wt %, glistenings tend to occur even by a slight temperature change. The water absorptivity is preferably at least 1.6 wt %, so that glistenings scarcely occur even if the temperature change is large. On the other hand, if the water absorptivity exceeds 4.5 wt %, the flexibility tends to decrease, and the shape restoration property tends to decrease, although no glistening problem will occur. The water absorptivity is preferably at most 4.4 wt %, so that the decrease in the flexibility or the decrease in the shape restoration property tends to be less likely to occur.

In the present invention, the water absorptivity is a value obtained by the following formula.

$$\text{Water absorptivity (wt \%)} = \{(W-W_0)/W_0\} \times 100$$

This is a value with respect to a test specimen having a thickness of 1.0 mm at 25° C. In the formula, W is the weight (g) of the test specimen upon absorption of water to the equilibrium state, and $W_0$ is the weight (g) of the test specimen in a dried state.

The soft intraocular lens material of the present invention is one having an excellent property such that no glistenings will occur even when a temperature change occurs, as mentioned above. Such a temperature change is a temperature change within a range of a usual environmental temperature at which the intraocular lens is used, i.e. a range including a common body temperature of from 36 to 37° C. For example, it may be a temperature change of about 15° C. from about 40° C. to about 25° C., or at least a temperature change of about 5° C. from about 40° C. to about 35° C.

As described in the foregoing, the soft intraocular lens material of the present invention is excellent in flexibility and has a high refractive index, whereby the lens can be made thin and can be folded and inserted through a small incision. Further, it is a soft intraocular lens material which is excellent in transparency and free from glistenings.

Now, the soft intraocular lens material of the present invention will be described in further detail with reference to Examples. However, it should be understood that the present invention is by no means restricted to such specific Examples.

EXAMPLE 1 TO 21 AND COMPARATIVE EXAMPLES 1 to 6

The polymerizable components as identified in Table 1 or 2 and 1 part by weight, per 100 parts by weight of the total amount of the polymerizable components, of 2,2'-azobis(2,4-dimethylvaleronitrile), as a polymerization initiator, were mixed, and the mixture was poured into a casting mold having a desired intraocular lens shape. This casting mold was put into an oven and heat polymerization molding was carried out at 50° C. for 24 hours. Then, the casting mold was transferred to an air circulating dryer and heated to from 65 to 130° C. at a rate of 10° C./hr and then cooled to room temperature. Then, light irradiation was carried out over one hour by means of an irradiation apparatus (black light, manufactured by Matsushita Electric Industrial Co., Ltd.). Thereafter, the obtained polymer was taken out from the casting mold and further dried for 2 days at 50° C. in an oven to obtain a soft intraocular lens material having a thickness of 1 mm.

Abbreviations used in Tables 1 and 2 are as follows.
(Meth)acrylate (A)
    POEA: 2-Phenoxyethyl acrylate
    POEMA: 2-Phenoxyethyl methacrylate
    PEA: Phenylethyl acrylate
    PEMA: Phenylethyl methacrylate

TABLE 1

| Example No. | Polymerizable components (parts by weight) | | | | | | | |
|---|---|---|---|---|---|---|---|---|
| | (Meth)acrylate (A) | | Hydrophilic monomer (B) | | Alkyl (meth)acrylate (C) | | Crosslinkable monomer (D) | |
| 1 | POEA | (20) | HEMA | (15) | EA | (80) | EDMA | (4) |
| 2 | POEA | (20) | HEMA | (25) | EA | (80) | EDMA | (4) |
| 3 | POEA | (40) | HEMA | (15) | EA | (60) | BDDA | (4) |
| 4 | POEA | (40) | HEMA | (25) | EA | (60) | EDMA | (4) |
| 5 | POEA | (60) | HEMA | (15) | EA | (40) | BDDA | (4) |
| 6 | POEA | (60) | HEMA | (15) | EA | (40) | EDMA | (4) |
| 7 | POEA | (60) | HEMA | (15) | EA | (40) | BDDMA | (4) |
| 8 | POEA | (60) | HEMA | (20) | EA | (40) | BDDA | (4) |
| 9 | POEA | (60) | HEMA | (25) | EA | (40) | BDDA | (4) |
| 10 | POEA | (60) | HEMA | (30) | 3FEA | (40) | EDMA | (2) |
| 11 | POEA | (60) | HEMA | (40) | EA | (40) | BDDA | (4) |
| 12 | POEA | (60) | HEA | (15) | EA | (40) | BDDA | (4) |
| 13 | POEA | (60) | HEA | (25) | EA | (40) | BDDA | (4) |

TABLE 2

| Example No. | Polymerizable components (parts by weight) | | | | | | | |
|---|---|---|---|---|---|---|---|---|
| | (Meth)acrylate (A) | | Hydrophilic monomer (B) | | Alkyl (meth)-acrylate (C) | | Crosslinkable monomer (D) | |
| 14 | POEA | (60) | NVP | (15) | EA | (40) | BDDA | (4) |
| 15 | POEA | (60) | NVP | (25) | EA | (40) | BDDA | (4) |
| 16 | POEA | (60) | DMAA | (15) | EA | (40) | BDDA | (5) |
| 17 | POEA | (60) | DMAA | (25) | EA | (40) | BDDA | (4) |
| 18 | POEA | (60) | HBMA | (30) | EA | (40) | BDDA | (4) |
| 19 | POEA | (70) | HEMA | (15) | EA | (30) | BDDA | (4) |
| 20 | POEMA | (30) | HEMA | (15) | EA | (70) | BDDA | (2) |
| 21 | — | | HEMA | (20) | iBuA | (80) | — | |
| Comp. Ex. | | | | | | | | |
| 1 | POEA | (60) | — | | EA | (40) | BDDA | (4) |
| 2 | POEA | (60) | — | | 3FEA | (40) | EDMA | (2) |
| 3 | POEA | (60) | HEMA | (6) | 3FEA | (40) | EDMA | (2) |
| 4 | PEA PEMA | (67) (33) | — | | — | | BDDA | (3.5) |
| 5 | POEA | (60) | HEMA | (10) | EA | (40) | BDDA | (4) |
| 6 | POEA | (60) | HEMA | (60) | EA | (40) | BDDA | (4) |

Hydrophilic Monomer (B)
    HEMA: 2-Hydroxyethyl methacrylate
    HEA: 2-Hydroxyethyl acrylate
    NVP: N-Vinylpyrrolidone
    DMAA: N,N-Dimethylacrylamide
    HBMA: 2-Hydroxybutyl methacrylate
Alkyl (Meth)Acrylate (C)
    EA: Ethyl acrylate
    iBuA: Isobutyl acrylate
    3FEA: 2,2,2-Trifluoroethyl acrylate
Crosslinkable Monomer (D)
    BDDA: Butanediol diacrylate
    EDMA: Ethylene glycol dimethacrylate
    BDDMA: Butanediol dimethacrylate The amounts of the hydrophilic monomer (B) and the crosslinkable monomer (D) in Tables 1 and 2 are amounts by parts by weight per 100 parts by weight of the total amount of the (meth)acrylate (A) and the alkyl (meth)acrylate (C). However, in Example 21, the sum of the hydrophilic monomer (B) and the alkyl (meth)acrylate (C) becomes 100 wt %.

Then, as the physical properties of the obtained soft intraocular lens materials, the water absorptivity, the transparency (evaluation of glistenings), the flexibility and the shape restoration property were examined in accordance with the following methods. The results are shown in Table 3.

(a) Water absorptivity

A test specimen having a thickness of 1.0 mm was prepared from the soft intraocular lens material, and the water absorptivity of this test specimen at 25° C. was obtained by the following formula.

$$\text{Water absorptivity (wt \%)} = \{(W-W_0)/W_0\} \times 100$$

wherein W is the weight (g) of the test specimen upon absorption of water to the equilibrium state, and $W_0$ is the weight (g) of the test specimen in a dried state.

(b) Transparency (evaluation of glistenings)

The soft intraocular lens material was immersed in water at 40° C. for 3 hours and then in water at 25° C. or 35° C. for 1 hour, whereupon the appearance (transparency) of this soft intraocular lens material was visually observed under irradiation of a transmitted light by means of a projector (V-12B, manufactured by Nikon K.K.), and evaluated on the basis of the following evaluation standards.

Evaluation Standards

A: Excellent transparency was maintained even after a temperature change from 40° C. to 25° C. in water.
B: Slight turbidity was observed after a temperature change from 40° C. to 25° C. in water, but excellent transparency was maintained after a temperature change from 40° C. to 35° C.
C: Turbidity was remarkable after a temperature change from 40° C. to 25° C. in water, and turbidity was observed even after a temperature change from 40° C. to 35° C.
D: Turbidity was remarkable even after a temperature change from 40° C. to 35° C. in water.
E: Irrespective of the temperature change, the material was turbid and opaque from the beginning.

Such evaluation of glistenings was carried out based on the temperature change which is believed to take place in the eye when the intraocular lens is actually implanted in the eye of a human being by an ophthalmic surgery. Namely, when an intraocular lens at room temperature, is implanted in the eye of a human being, the temperature in the eye rises to about 40° C. by inflammation, and when the inflammation ceases, the temperature in the eye recovers and lowers to the body temperature, whereby the intraocular lens is considered to undergo glistenings. Accordingly, glistenings were examined during the temperature drop from such 40° C. to 35° C. or 25° C., which is larger than the temperature drop to a usual body temperature of from 36 to 37° C.

(c) Flexibility

The soft intraocular lens material in a dried state was folded into two at 25° C. by means of tweezers, whereupon the folded state was evaluated in accordance with the following evaluation standards.

Evaluation Standards

A: It can be readily folded without exerting any extra force.
B: It can be readily folded by exerting a slight force.
C: It can be folded, but a substantial extra force is required.
D: It can hardly be folded.

(d) Shape restoration property

The soft intraocular lens material was folded back into two by means of tweezers, and held in that state for 1 minute, whereupon the material was released, and the state at that time was evaluated in accordance with the following evaluation standards.

Evaluation Standards

A: The time required to recover to the initial shape, was less than 30 seconds.
B: The time required to recover to the initial shape was at least 30 seconds and less than 1 minute.
C: The time required to recover to the initial shape was at least 1 minute and less than 3 minute.
D: The time required to recover to the initial shape was at least 3 minutes, or the material was not recovered to the initial shape.

TABLE 3

Physical properties of soft intraocular lens materials

| Example No. | Water absorptivity (wt %) | Transparency (evaluation of glistening) | Flexibility | Shape restoration property |
| --- | --- | --- | --- | --- |
| 1 | 2.3 | A | A | A |
| 2 | 3.5 | A | A | A |
| 3 | 2.1 | A | A | A |
| 4 | 3.3 | A | A | A |
| 5 | 1.7 | A | A | A |
| 6 | 1.8 | A | A | A |
| 7 | 1.8 | A | A | A |
| 8 | 2.2 | A | A | A |
| 9 | 2.7 | A | A | A |
| 10 | 2.5 | A | B | B |
| 11 | 4.4 | A | B | B |
| 12 | 1.8 | B | A | A |
| 13 | 2.8 | A | A | A |
| 14 | 2.4 | A | B | B |
| 15 | 3.9 | A | B | B |
| 16 | 2.3 | A | B | B |
| 17 | 4.1 | A | B | B |
| 18 | 1.7 | B | A | A |
| 19 | 1.7 | A | A | A |
| 20 | 2.0 | A | A | B |
| 21 | 2.3 | A | A | A |
| Comparative Example No. | | | | |
| 1 | 0.4 | C | A | A |
| 2 | 0.3 | C | A | A |
| 3 | 0.7 | C | A | A |
| 4 | 0.4 | C | A | A |
| 5 | 1.1 | C | A | A |
| 6 | 6.9 | A | C | C |

It is evident from the results shown in Table 3 that the soft intraocular lens materials obtained in Examples 1 to 21 have water absorptivities of from 1.7 to 4.4 wt %, whereby excellent transparency is maintained without glistenings, even after a temperature drop of from 5 to 15° C., and they are excellent also in the flexibility and the shape restoration properties.

Particularly, it is evident that in Examples 1 to 11 and 19 to 21, wherein 2-hydroxyethyl methacrylate is used as the hydrophilic monomer (B), the obtained soft intraocular lens materials are free from glistenings even after a temperature drop of 15° C.

Whereas, with the soft intraocular lens materials obtained in Comparative Examples 1 to 5, the water absorptivity of each of them is less than 1.5 wt %, and formation of glistening is remarkable.

Further, with the material obtained in Comparative Example 6, the water absorptivity exceeds 4.5 wt %, and it is inferior in the flexibility and the shape restoration property, although no formation of glistenings is observed.

Further, in Comparative Examples 3 and 5, glistenings were observed in spite of the fact that the hydrophilic monomer (B) was used. Accordingly, it is evident that the effect to suppress formation of glistenings, is obtainable when the material has units derived from the hydrophilic monomer (B), and the water absorptivity has a specific value of from 1.5 to 4.5 wt %, particularly at least 1.5 wt %.

Then, dumbbell-shaped test specimens were prepared from the soft intraocular lens materials obtained in Example 5 and Comparative Example 4, and tensile tests of the test specimens were carried out at a tensile speed of 100 mm/min by means of a tensile strength tester (Model 4301, manufactured by INSTRON Japan K.K.), whereby the elongation (%) at breakage was measured.

As a result, the elongation of the test specimen of Example 5 was 143%, and that of the test specimen of Comparative Example 4 was 94%. Thus, it is evident that the soft intraocular lens material of Example 5 is excellent in flexibility and has good mechanical strength.

As described in the foregoing, the soft intraocular lens material of the present invention is excellent in flexibility and has a high refractive index, whereby the lens can be made thin and can be folded and inserted from a small incision, and yet it is capable of presenting a soft intraocular lens which is excellent in transparency and free from glistenings.

What is claimed is:

1. A soft intraocular lens material which consists essentially of a polymer obtained by polymerizing polymerizable components, wherein said polymer has a water absorptivity of from 1.5 to 4.5 wt %, and wherein said polymerizable components comprise:

(A) an aromatic ring-containing (meth)acrylate of the formula (I):

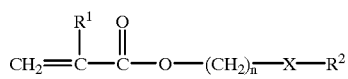

(I)

wherein $R^1$ is a hydrogen atom or a methyl group, $R^2$ is an aromatic group wherein hydrogen atoms may be substituted by substituents, X is an oxygen atom or a direct bond, and n is an integer of from 0 to 5;

(B) at least one hydrophilic monomer selected from the group consisting of hydroxyl group-containing alkyl (meth)acrylates wherein the alkyl group has from 1 to 20 carbon atoms, (meth)acrylamide monomers, and N-vinyl lactams;

(C) an alkyl (meth)acrylate wherein the alkyl group has from 1 to 20 carbon atoms, other than the above hydroxyl group-containing alkyl (meth)acrylate wherein the alkyl group has from 1 to 20 carbon atoms; and (D) a crosslinkable monomer.

2. The soft intraocular lens material according to claim 1, wherein said hydrophilic monomer is a hydroxyl group-containing alkyl (meth)acrylate wherein the alkyl group has from 1 to 20 carbon atoms.

3. The soft intraocular lens material according to claim 2, wherein said hydroxyl group-containing alkyl (meth) acrylate wherein the alkyl group has from 1 to 20 carbon atoms is selected from the group consisting of hydroxyethyl (meth)acrylate, hydroxypropyl (meth)acrylate, hydroxybutyl (meth)acrylate, hydroxypentyl (meth)acrylate, dihydroxypropyl (meth)acrylate, dihydroxybutyl (meth)acrylate, and dihydroxypentyl (meth)acrylate.

4. The soft intraocular lens material according to claim 1, wherein said hydrophilic monomer is 2-hydroxyethyl methacrylate.

5. The soft intraocular lens material according to claim 1, wherein said hydrophilic monomer is a (meth)acrylamide monomer.

6. The soft intraocular lens material according to claim 5, wherein said (meth)acrylamide monomer is selected from the group consisting of N,N-dimethyl (meth)acrylamide, N,N-diethyl (meth)acylamide, N,N-dipropyl (meth) acrylamide, N,N-dimethylaminopropyl (meth)acrylamide, and N,N-diethylaminopropyl (meth)acrylamide.

7. The soft intraocular lens material according to claim 1, wherein said hydrophilic monomer is an N-vinyl lactam.

8. The soft intraocular lens material according to claim 7, wherein said N-vinyl lactam is selected from the group consisitng of N-vinylpyrrolidone, N-vinylpiperidone, and N-vinylcaprolactam.

9. The soft intraocular lens material according to claim 1, wherein said polymerizable components comprise said hydrophilic monomer in an amount of from 7 wt % to 45 wt %.

10. The soft intraocular lens material according to claim 1, wherein said aromatic ring-containing (meth)acrylate (A) of the formula (I) is at least one member selected from the group consisting of phenoxyethyl acrylate, phenylethyl acrylate, and benzyl acrylate.

11. The soft intraocular lens material according to claim 10, wherein said aromatic ring-containing (meth)acrylate (A) of the formula (I) is phenoxyethyl acrylate.

12. The soft intraocular lens material according to claim 10, wherein said aromatic ring-containing (meth)acrylate (A) of the formula (I) is phenylethyl acrylate.

13. The soft intraocular lens material according to claim 10, wherein said aromatic ring-containing (meth)acrylate (A) of the formula (I) is benzyl acrylate.

14. The soft intraocular lens material according to claim 1, wherein said alkyl (meth)acrylate (C) wherein the alkyl group has from 1 to 20 carbon atoms, other than the hydroxyl group-containing alkyl (meth)acrylate wherein the alkyl group has from 1 to 20 carbon atoms, is selected from the group consisting of ethyl acrylate and butyl acrylate.

15. The soft intraocular lens material according to claim 14, wherein said alkyl (meth)acrylate (C) wherein the alkyl group has from 1 to 20 carbon atoms, other than the hydroxyl group-containing alkyl (meth)acrylate wherein the alkyl group has from 1 to 20 carbon atoms, is ethyl acrylate.

16. The soft intraocular lens material according to claim 14, wherein said alkyl (meth)acrylate (C) wherein the alkyl group has from 1 to 20 carbon atoms, other than the hydroxyl group-containing alkyl (meth)acrylate wherein the alkyl group has from 1 to 20 carbon atoms, is butyl acrylate.

17. The soft intraocular lens material according to claim 1, wherein said crosslinkable monomer (D) is selected from the group consisting of butanediol di(meth)acrylate and ethylene glycol di(meth)acrylate.

18. The soft intraocular lens material according to claim 17, wherein said crosslinkable monomer (D) is butanediol di(meth)acrylate.

19. The soft intraocular lens material according to claim 17, wherein said crosslinkable monomer (D) is ethylene glycol di(meth)acrylate.

20. The soft intraocular lens material according to claim 1, wherein said material further comprises an ultraviolet absorber and/or a yellow or orange dyestuff.

\* \* \* \* \*